United States Patent [19]

Ondetti et al.

[11] 4,217,458
[45] Aug. 12, 1980

[54] ACYLMERCAPTOACYL DERIVATIVES OF 4,5-DIHYDRO-1H-PYRROLE-2-CARBOXYLIC ACIDS AND 1,4,5,6-TETRAHYDROPYRIDINE-2-CARBOXYLIC ACIDS

[75] Inventors: Miguel A. Ondetti, Princeton; Michael E. Condon, Lawrenceville, both of N.J.

[73] Assignee: E. R. Squibb & Sons, Inc., Princeton, N.J.

[21] Appl. No.: 69,418

[22] Filed: Aug. 24, 1979

Related U.S. Application Data

[63] Continuation-in-part of Ser. No. 967,827, Dec. 8, 1978.

[51] Int. Cl.² .................. C07D 213/55; C07D 207/22
[52] U.S. Cl. .............................. 546/326; 260/326.43
[58] Field of Search .................... 546/326; 260/326.43

[56] References Cited

U.S. PATENT DOCUMENTS

| | | | |
|---|---|---|---|
| 4,129,566 | 12/1978 | Ondetti et al. | 546/326 |
| 4,154,942 | 5/1979 | Ondetti et al. | 546/326 |

*Primary Examiner*—Alan L. Rotman
*Attorney, Agent, or Firm*—Lawrence S. Levinson; Stephen B. Davis

[57] ABSTRACT

New acylmercaptoacyl derivatives of 4,5-dihydro-1H-pyrrole-2-carboxylic acids and 1,4,5,6-tetrahydropyridine-2-carboxylic acids having the general formula

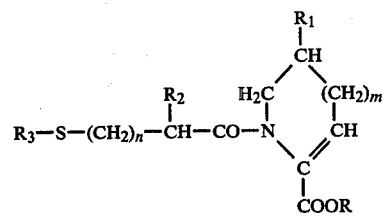

are useful as hypotensive agents.

8 Claims, No Drawings

ACYLMERCAPTOACYL DERIVATIVES OF 4,5-DIHYDRO-1H-PYRROLE-2-CARBOXYLIC ACIDS AND 1,4,5,6-TETRAHYDROPYRIDINE-2-CARBOXYLIC ACIDS

RELATED APPLICATIONS

This application is a continuation-in-part of Ser. No. 967,827 filed Dec. 8, 1978.

SUMMARY OF THE INVENTION

This invention relates to new mercaptoacyl derivatives of 4,5-dihydro-1H-pyrrole-2-carboxylic acids and 1,4,5,6-tetrahydropyridine-2-carboxylic acids (2,3-dehydropipecolic acids) which have the formula (I)

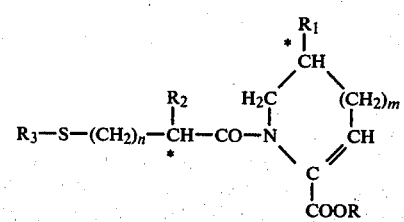

wherein

R is hydrogen or lower alkyl;
$R_1$ is hydrogen, hydroxy, halogen or lower alkoxy;
$R_2$ is hydrogen or lower alkyl;
$R_3$ is hydrogen, an acyl group

or

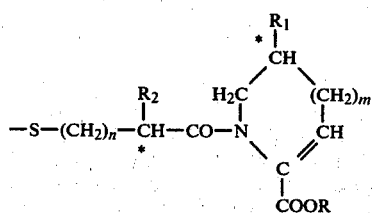

m and n each is 0 or 1;
and to salts thereof.

The asterisks indicate centers of asymmetry. The carbon atom is asymmetric when $R_1$ or $R_2$ are other than hydrogen.

BACKGROUND OF THE INVENTION

In copending application Ser. No. 878,144, filed Feb. 15, 1978, by Miguel Angel Ondetti and Sesha Iyer Natarajan, now U.S. Pat. No. 4,129,566, there are described derivatives of 3,4-dehydroproline and 4,5-dehydropipecolic acid which have the formula

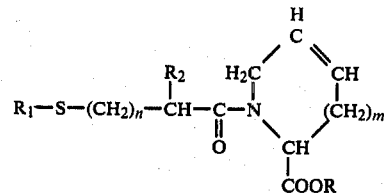

wherein
R and $R_2$ each is hydrogen or lower alkyl;
$R_1$ is hydrogen, lower alkanoyl or

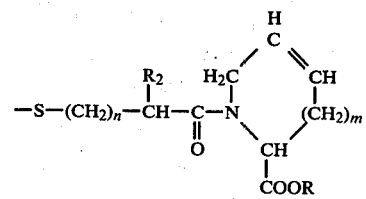

m and n each is 0 or 1,
and to salts thereof.

These compounds, it will be observed, have a double bond between the second and third carbons from the nitrogen in a clockwise direction, carbons not attached to the carboxy group. These compounds are obtained from starting materials with the formula

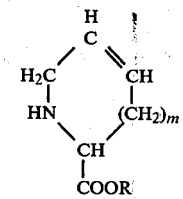

The compounds of this invention are distinguishable by a double bond joining the carbon bearing the carboxy group and its adjacent carbon, carbons more distant from the nitrogen in a clockwise direction. Such compounds are not obtainable by the methods described in the prior application. We have found that the compounds of this invention can be obtained by a different route described below and furthermore similar $R_1$-substituted compounds of this description can be obtained whereas only ring unsubstituted compound of the prior type are available.

DETAILED DESCRIPTION OF THE INVENTION

This invention relates to mercaptoacyl derivatives of 4,5-dihydro-1H-pyrrole-2-carboxylic acids and 1,4,5,6-tetrahydropyridine-2-carboxylic acids, and salts thereof, which have formula I above.

Within the class described, there are especially preferred those compounds of formula I wherein R is hydrogen or lower alkyl, especially hydrogen or t-butyl; $R_1$ is hydrogen, hydroxy or halogen, especially hydrogen; $R_2$ is hydrogen or lower alkyl, especially hydrogen or methyl; $R_3$ is hydrogen or lower alkanoyl, especially hydrogen or acetyl; m is 0 and n is 1.

The lower alkyl groups represented by the symbols are straight or branched chain hydrocarbon radicals having up to 7 carbon atoms, e.g., methyl, ethyl, propyl, isopropyl, butyl, isobutyl, t-butyl and the like. The lower alkoxy groups are of the same type, e.g., methoxy, ethoxy, propoxy, isobutoxy, etc. The $C_1$-$C_4$ members, especially $C_1$ and $C_2$ members, are preferred.

$R_4$ is lower alkyl of 1 to 6 carbons, cycloalkyl of 3 to 7 carbons, an aryl group such as

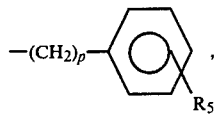

or a hetero group such as

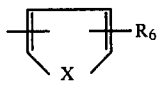

or

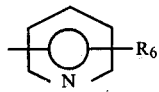

wherein p is zero, one or two; $R_5$ is hydrogen, lower alkyl of 1 to 4 carbons, especially methyl, lower alkoxy of 1 to 4 carbons, especially methoxy, halogen, or lower alkylthio, especially methylthio; X is O or S; and $R_6$ is hydrogen, lower alkyl of 1 to 4 carbons, especially methyl, or halogen. Preferred acyl groups

are those which can be removed by conventional hydrolysis or ammonolysis. These preferred acyl groups are the lower alkanoyl groups having from 2 to 4 carbons and benzoyl with acetyl being especially preferred.

The halogens are the four common halogens, fluorine being preferred.

The compounds of formula I are produced by the addition of an acid chloride having the formula

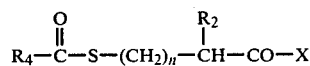 (II)

wherein X is halogen, preferably chlorine, to the dehydroimino acid ester having the formula

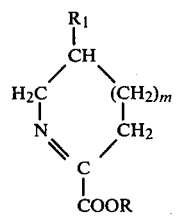 (III)

wherein R is lower alkyl, in an inert organic solvent like dichloromethane, chloroform, benzene, toluene or the like at a reduced temperature, e.g., in the range of about −5° to +5° C., to give the intermediate having the formula

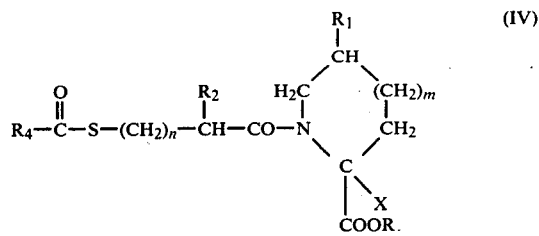 (IV)

The intermediate of formula IV, which need not be isolated, is dehalogenated, e.g., with a strong base such as 1,5-diazabicyclo-[5.4.0]undec-5-ene in an inert organic solvent like dichloromethane, chloroform, benzene, toluene at a reduced temperature, e.g., in the range of about −5° to +5° C. to give a compound of formula I wherein R is lower alkyl and $R_3$ is

To obtain the compound of formula I wherein R is hydrogen, the ester can be treated with trifluoroacetic acid and anisole when R is the preferred t-butyl.

Treatment with a base like aqueous ammonia or sodium hydroxide removes the acyl

group.

To obtain the bis compound or "dimer" of formula I, i.e., wherein $R_3$ is the radical

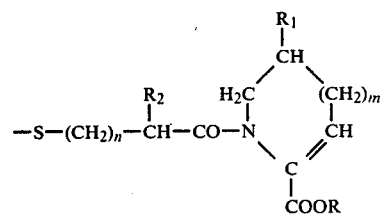

the corresponding compound wherein $R_3$ is hydrogen is directly oxidized, e.g., with alcoholic iodine solution. Alternatively the dehydro imino acid ester of formula III is acylated with dithio dialkanoyl chloride having the formula

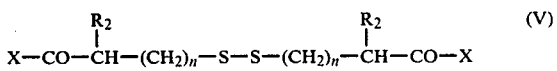 (V)

wherein X is halogen, preferably chlorine, and $R_2$ and n have the same meaning as above.

The starting materials of formula III are obtained by N-chlorination of the imino acid ester with tert.-butyl hypochlorite followed by dehydrohalogenation with a strong base, e.g., sodium or potassium alkoxides.

The products of formula I have centers of asymmetry indicated by the asterisk in formula I. The compounds accordingly exist in stereoisomeric forms or in racemic mixtures thereof. All of these are within the scope of the invention. The starting material can be in the form of one of the enantiomers or racemic mixtures thereof. When the product is in the form of a racemate, the stereoisomers can be separated by conventional chromatographic or fractional crystallization methods.

Alternatively the optically active form of the acyl side chain, the dehydro imino acid ester or both can be used in the synthetic procedures to obtain the stereoisomeric form desired.

The compounds of this invention from basic salts with various inorganic and organic bases which are also within the scope of the invention. Such salts include ammonium salts, alkali metal salts like sodium and potassium salts (which are preferred), alkaline earth metal salts like the calcium and magnesium salts, salts with organic bases, e.g., dicyclohexylamine salt, benzathine, N-methyl-D-glucamine, hydrabamine, salts with amino acids like arginine, lysine and the like. The non-toxic, physiologically acceptable salts are preferred, although other salts are also useful, e.g., in isolating or purifying the product.

The salts are formed in conventional manner by reacting the free acid form of the product with one or more equivalents of the appropriate base providing the desired cation in a solvent or medium in which the salt is insoluble, or in water and removing the water by freeze drying. By neutralizing the salt with an insoluble acid like a cation exchange resin in the hydrogen form (e.g., polystyrene sulfonic acid resin like Dowex 50) or with an aqueous acid, and extraction with an organic solvent, e.g., ethyl acetate, dichloromethane or the like, the free acid form can be obtained, and, if desired, another salt formed.

Additional experimental details are found in the examples which are preferred embodiments and also serve as models for the preparation of other members of the group.

The compounds of this invention are useful as hypotensive agents. They inhibit the conversion of the decapeptide angiotensin I to angiotensin II by angiotensin converting enzyme and therefore are useful in reducing or relieving angiotensin related hypertension. Thus by the administration of a composition containing one or a combination of compounds of formula I or physiologically acceptable salt thereof, angiotensin dependent hypertension in the species of mammal suffering therefrom, e.g., in mice, rats, dogs, cats, etc., is alleviated or reduced. A single dose, or preferably two to four divided daily doses, provided on a basis of about 0.1 to 100 mg. per kilogram per day, preferably about 1 to 50 mg. per kilogram per day is appropriate to reduce blood pressure as indicated in the animal model experiments described by S. L. Engel, T. R. Schaeffer, M. H. Waugh and B. Rubin, Proc. Soc. Exp. Biol. Med. 143, 483 (1973). The substance is preferably administered orally, but parenteral routes such as subcutaneously, intramuscularly, intravenously or intraperitoneally can also be employed.

The compounds of this invention can be utilized to achieve the reduction of blood pressure by formulating in compositions such as tablets, capsules or elixirs for oral administration (which is preferred) or in sterile solutions or suspensions for parenteral administration. About 10 to 500 mg. of a compound or mixture of compounds of formula I or physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The following examples are illustrative of the invention and constitute preferred embodiments. All temperatures are in degrees Celsius.

EXAMPLE 1

(±)-1-[3-(Acetylthio)-2-methyl-1-oxopropyl]-4,5-dihydro-1H-pyrrole-2-carboxylic acid (a) 1,2-Dehydroproline, t-butyl ester To a stirred solution of 34.2 g. (0.20 mole) of proline t-butyl ester in 600 ml. of ether at $-5°$ to $0°$ is added dropwise over ten minutes 21.7 g. (23.9 ml.=0.20 mole) of freshly prepared t-butyl hypochlorite [Org. Syn., Coll. Vol. V, 184 (1973)]. During the addition, the temperature is maintained at $-5°$ to $0°$. After the addition is complete, the solution is stirred at this temperature for an additional five minutes.

To the vigorously stirred solution is added rapidly ($\sim$3–5 min.) a solution of 7.8 g. (0.20 mole) of potassium in freshly distilled dry ($CaH_2$) t-butanol. After the addition, the temperature of the reaction mixture is about $18°$. The reaction vessel is removed from the cooling bath and stirred for thirty minutes. The reaction mixture is filtered through Celite (diatomaceous earth) and the filtrate concentrated in vacuo. The residue is taken up in ether and washed with several portions of water. The ether solution is dried and concentrated in vacuo to 36.1 g. of yellow liquid. A trace of hydroquinone is added and the crude product distilled, affording 22.4 g. of 1,2-dehydroproline, t-butyl ester (66%), b.p. $60°$–$62°$/0.1 mm.

(b) (±)-1-[3-(Acetylthio)-2-methyl-1-oxopropyl]-4,5-dihydro-1H-pyrrole-2-carboxylic acid, t-butyl ester To a stirred solution of 16.9 g. (0.10 mole) of freshly distilled 1,2-dehydroproline t-butyl ester in 60 ml. of dichloromethane at $-5°$ to $0°$ is added dropwise over ten minutes, a solution of 18.1 g. (0.1 mole) of 3-acetylthio-2-methylpropanoyl chloride in 60 ml. of dichloromethane. During the addition the temperature is maintained at $-5°$ to $0°$, and after the addition is complete the solution is stirred for five minutes.

To this stirred solution at $-5°$ to $0°$ is added dropwise over ten minutes a solution of 15.2 g. (0.10 mole) of 1,5-diazabicyclo[5.4.0]undec-5-ene in 60 ml. of dichloromethane. After the addition is complete, the cooled bath is removed, and the reaction mixture is stirred for one hour.

The yellow solution is washed with cold dilute hydrochloric acid, saturated aqueous sodium bicarbonate, dried, and concentrated in vacuo to 27.7 g. of oil. The oil is taken up in diisopropyl ether and chilled, affording 9.3 g. (30%) of crystalline solid (±)-1-[3-(acetylthio)-2-methyl-1-oxopropyl]-4,5-dihydro-1H-pyrrole-2-carboxylic acid, t-butyl ester, m.p. $77°$–$80°$.

(c) (±)-1-[3-(Acetylthio)-2-methyl-1-oxopropyl]-4,5-dihydro-1H-pyrrole-2-carboxylic acid To a stirred solution of 6.26 g. (20 mmoles) of the ester from part b in 22 ml. (21.6 g.=200 mmoles) of distilled anisole at $0°$–$5°$ is added 100 ml. of distilled trifluoroacetic acid (precooled to $0°$–$5°$). The resulting solution is stirred at $0°$–$5°$ for one hour.

The trifluoroacetic acid is removed in vacuo, the residue is taken up in ether, and this is thoroughly extracted with saturated aqueous sodium bicarbonate. The combined extracts are back-washed with ether, acidified with 10% aqueous potassium hydrogen sulfate, and this is thoroughly extracted with ethyl acetate. The combined extracts are dried and concentrated in vacuo to an oil which crystallizes on standing. Trituration of this solid with diisopropyl ether affords 4.45 g. (45%) of crystalline solid (±)-1-[3-(acetylthio)-2-methyl-1-oxopropyl]-4,5-dihydro-1H-pyrrole-2-carboxylic acid. Recrystallization of a 1.5 g. sample from ethyl acetatehexane affords an analytical sample (1.0 g.,) m.p. 83°–85°.

EXAMPLE 2

(±)-4,5-Dihydro-1-(3-mercapto-2-methyl-1-oxopropyl)-1H-pyrrole-2-carboxylic acid A mixture of 2.86 g. (11.2 mmoles) of (±)-1-[3-(acetylthio)-2-methyl-1-oxopropyl]-4,5-dihydro-1H-pyrrole-2-carboxylic acid, 15 ml. of concentrated ammonium hydroxide, and 15 ml. of water is stirred at 0°–5° under argon for fifteen minutes (a clear solution is obtained within two minutes). The solution is acidified with cold dilute hydrochloric acid, and thoroughly extracted with ethyl acetate. The combined extracts are dried and concentrated in vacuo to a solid, which gives 2.0 g. (83%) of crude (±)-4,5-dihydro-1-(3-mercapto-2-methyl-1-oxopropyl)-1H-pyrrole-2-carboxylic acid on trituration with ether. Recrystallization from ethyl acetate affords an analytical sample (0.80 g.), m.p. 112°–114°.

EXAMPLE 3

(±)-1-[3-(Acetylthio-2-methyl-1-oxopropyl]-4,5-dihydro-1H-pyrrole-2-carboxylic acid, methyl ester By substituting 1,2-dehydroproline methyl ester [Chem. Ber., 108, 2547 (1975)] in the procedure of Example 1b, (±)-1-[3-(acetylthio)-2-methyl-1-oxopropyl]-4,5-dihydro-1H-pyrrole-2-carboxylic acid, methyl ester is obtained as a chromatographically pure oil after chromatography on silica gel using 9:1 benzene-ethyl acetate as eluant. $R_f$=0.47 (silica gel, benzene:ethyl acetate, 1:1).

EXAMPLE 4

4,5-Dihydro-1-[2-(acetylthio)-1-oxoethyl]-1H-pyrrole-2-carboxylic acid methyl ester By substituting 2-acetylthioacetyl chloride for the 3-acetylthio-2-methylpropanoyl chloride in the procedure of Example 3, 4,5-dihydro-1-[2-(acetylthio)-1-oxoethyl]-1H-pyrrole-2-carboxylic acid methyl ester is obtained.

EXAMPLE 5

(±)-4,5-Dihydro-1-(2-mercapto-1-oxopropyl)-1H-pyrrole-2-carboxylic acid

By substituting 2-acetylthiopropanoyl chloride for the 3-acetylthio-2-methypropanoyl chloride in the procedure of Example 1 and then submitting the product of the procedure of Example 2, (±)-4,5-dihydro-1-(2-mercapto-1-oxopropyl)-1H-pyrrole-2-carboxylic acid is obtained.

EXAMPLE 6

(±)-4,5-Dihydro-1-(2-ethyl-3-mercapto-1-oxopropyl)-1H-pyrrole-2-carboxylic acid

By substituting 3-acetylthio-2-ethylpropanoyl chloride for the 3-acetylthio-2-methylpropanoyl chloride in the procedure of Example 1 and then submitting the product to the procedure of Example 2, (±)-4,5-dihydro-1-(2-ethyl-3-mercapto-1-oxopropyl)-1H-pyrrole-2-carboxylic acid is obtained.

EXAMPLE 7

(±)-1-[3-(Butyrylthio)-2-methyl-1-oxopropyl]-4,5-dihydro-1H-pyrrole-2-carboxylic acid By substituting 3-butyrylthio-2-methylpropanoyl chloride for the 3-acetylthio-2-methylpropanoyl chloride in the procedure of Example 1, (±)-1-[3-(butyrylthio)-2-methyl-1-oxopropyl]-4,5-dihydro-1H-pyrrole-2-carboxylic acid is obtained.

EXAMPLE 8

(±)-4,5-Dihydro-4-hydroxy-(3-mercapto-2-methyl-1-oxopropyl)-1H-pyrrole-2-carboxylic acid By substituting 4-tert-butoxy-L-proline tertbutyl ester [prepared from 4-tert-butoxy-L-hydroxy proline as described in J. Am. Chem. Soc., 82, 3359 (1960) for L-proline] for the L-proline tert-butyl ester in the procedure of Example 1 and then submitting the product to the procedure of Example 2, (±)-4,5-dihydro-4-hydroxy-(3-mercapto-2-methyl-1-oxopropyl)-1H-pyrrole-2-carboxylic acid is obtained.

EXAMPLE 9

1-(3-Acetylthio-1-oxopropyl)-4,5-dihydro-4-hydroxy-1H-pyrrole-2-carboxylic acid

By substituting 4-tert-butoxy-L-proline tertbutyl ester for the L-proline tert-butyl ester and 3-acetylthiopropanoyl chloride for the 3-acetylthio-2-methylpropanoyl chloride in the procedure of Example 1, 1-(3-acetylthio-1-oxopropyl)-4,5-dihydro-4-hydroxy-1H-pyrrole-2-carboxylic acid is obtained.

EXAMPLE 10

(±)-4,5-Dihydro-4-hydroxy-1-(2-mercapto-1-oxopropyl)-1H-pyrrole-2-carboxylic acid By substituting 4-tert-butoxy-L-proline tertbutyl ester for the L-proline tert-butyl ester in the procedure of Example 5, (±)-4,5-dihydro-4-hydroxy-1-(2-mercapto-1-oxopropyl)-1H-pyrrole-2-carboxylic acid is obtained.

EXAMPLE 11

(±)-1-[3-(Acetylthio)-2-methyl-1-oxopropyl]-4,5-dihydro-4-fluoro-1H-pyrrole-2-carboxylic acid By substituting 4-fluoroproline tert-butyl ester [prepared from 4-fluoro-L-proline by the procedure described in J. Am. Chem. Soc., 82, 3359 (1960) for L-proline] for the L-proline tert-butyl ester in the procedure of Example 1, (±)-1-[3-(acetylthio)-2-methyl-1-oxopropyl]-4,5-dihydro-4-fluoro-1H-pyrrole-2-carboxylic acid is obtained.

EXAMPLE 12

(±)-4,5-Dihydro-4-fluoro-(3-mercapto-2-methyl-1-oxopropyl)-1H-pyrrole-2-carboxylic acid By substituting (±)-1-[3-(acetylthio)-2-methyl-1-oxopropyl]-4,5-dihydro-4-fluoro-1H-pyrrole-2-carboxylic acid for the (±)-1-[3-(acetylthio)-2-methyl-1-oxopropyl]-4,5-dihydro-1H-pyrrole-2-carboxylic acid in the procedure of Example 2, (±)-4,5-dihydro-4-fluoro-(3-mercapto-2-methyl-1-oxopropyl)-1H-pyrrole-2-carboxylic acid is obtained.

EXAMPLE 13

4,5-Dihydro-4-chloro-1-(2-mercaptoacetyl)-1H-pyrrole-2-carboxylic acid

By substituting 4-chloro-L-proline tertbutyl ester [prepared from 4-chloro-L-proline by the procedure described in J. Am. Chem. Soc., 82, 3359 (1960) for L-proline] for the L-proline tert-butyl ester and the 2-acetylthioacetyl chloride for the 3-acetylthio-2-methylpropanoyl chloride in the procedure of Example 1 and then submitting the product to the procedure of Example 2, 4,5-dihydro-4-chloro-1-(2-mercaptoacetyl)-1H-pyrrole-2-carboxylic acid is obtained.

EXAMPLE 14

4,5-Dihydro-1-(3-mercapto-1-oxopropyl)-4-methoxy-1H-pyrrole-2-carboxylic acid

By substituting 4-methoxy-L-proline tertbutyl ester [prepared from 4-methoxy-L-proline by the procedure described in J. Am. Chem. Soc., 82, 3359 (1960) for L-proline] for the L-proline tert-butyl ester and 3-acetylthiopropanoyl chloride for the 3-acetylthio-2-methylpropanoyl chloride in the procedure of Example 1, and then submitting the product to the procedure of Example 2, 4,5-dihydro-1-(3-mercapto-1-oxopropyl)-4-methoxy-1H-pyrrole-2-carboxylic acid is obtained.

EXAMPLE 15

(±)-4,5-Dihydro-4-ethoxy-(2-mercapto-1-oxopropyl)-1H-pyrrole-2-carboxylic acid

By substituting 4-ethoxy-L-proline tert-butyl ester [prepared from 4-ethoxy-L-proline by the procedure described in J. Am. Chem. Soc., 82, 3359 (1960) for L-proline] for the L-proline tert-butyl ester and acetylthioacetyl chloride for the 3-acetylthio-2-methylpropanoyl chloride in the procedure of Example 1, and then submitting the product to the procedure of Example 2, (±)-4,5-dihydro-4-ethoxy-(2-mercapto-1-oxopropyl)-1H-pyrrole-2-carboxylic acid is obtained.

EXAMPLE 16

(±)-4,5-Dihydro-1-(3-mercapto-2-methyl-1-oxopropyl)-1H-pyrrole-2-carboxylic acid, sodium salt A mixture of (±)-4,5-dihydro-1-(3-mercapto-2-methyl-1-oxopropyl)-1H-pyrrole-2-carboxylic acid and sodium bicarbonate in equimolar amounts is dissolved in water, and the solution is freezedried to give (±)-4,5-dihydro-1-(3-mercapto-2-methyl-1-oxopropyl)-1H-pyrrole-2-carboxylic acid, sodium salt.

EXAMPLE 17

1,1'-[Dithiobis-(±)-2-methyl-1-oxopropane-3,1-diyl)]-bis-4,5-dihydro-1H-pyrrole-2-carboxylic acid To a solution of (±)-4,5-dihydro-1-(3-mercapto-2-methyl-1-oxopropyl)-1H-pyrrole-2-carboxylic acid, sodium salt, in water, a solution of iodine in ethanol is added dropwise while maintaining the pH between 6 and 7 by careful addition of dilute sodium hydroxide. When a yellow permanent color is obtained, a few drops of an aqueous solution of sodium thiosulfate is added and the pH is lowered to 2-3 by addition of concentrated hydrochloric acid. The aqueous mixture is extracted with ethyl acetate and the organic phase is dried and concentrated to dryness in vacuo to give 1,1'-[dithiobis-(±)-2-methyl-1-oxopropane-3,1-diyl)]-bis-4,5-dihydro-1H-pyrrole-2-carboxylic acid.

EXAMPLE 18

4,5-Dihydro-1-(3-acetylthio)-1-oxopropyl)-4-methoxy-1H-pyrrole-2-carboxylic acid, methyl ester By substituting 4-methoxy-L-proline methyl ester for the L-proline methyl ester in the procedure of Example 3, 4,5-dihydro-1-(3-acetylthio)-1-oxopropyl)-4-methoxy-1H-pyrrole-2-carboxylic acid, methyl ester is obtained.

EXAMPLE 19

2,3-Dehydro-1-(3-acetylthio-1-oxopropyl)pipecolic acid ethyl ester

By substituting L-pipecolic acid ethyl ester for the proline tert-butyl ester and 3-acetylthiopropanoyl chloride for the 3-acetylthio-2-methylpropanoyl chloride in the procedure of Example 1, 2,3-dehydro-1-(3-acetylthio-1-oxopropyl)pipecolic acid ethyl ester is obtained.

EXAMPLE 20

2,3-Dehydro-1-(3-mercapto-1-oxopropyl)pipecolic acid

By substituting L-pipecolic acid tert-butyl ester [prepared from pipecolic acid by the procedure described in J. Am. Chem. Soc., 82, 3359 (1960) for L-proline] for the proline tert-butyl ester and 3-acetylthiopropanoyl chloride for the 3-acetylthio-2-methyl propanol chloride in the procedure of Example 1 and then submitting the product to the procedure of Example 2, 2,3-dehydro-1-(3-mercapto-1-oxopropyl)pipecolic acid is obtained.

EXAMPLE 21

(±)-2,3-Dehydro-1-(3-mercapto-2-methyl-1-oxopropyl)-pipecolic acid

By substituting pipecolic acid tert-butyl ester for the L-proline tert-butyl ester in the procedure of Example 1, and then submitting the product to the procedure of Example 2, (±)-2,3-dehydro-1-(3-mercapto-2-methyl-1-oxopropyl)pipecolic acid is obtained.

EXAMPLE 22

(±)-2,3-Dehydro-1-(3-acetylthio-2-ethyl-1-oxopropyl)-pipecolic acid

By substituting pipecolic acid tert-butyl ester for the L-proline tert-butyl ester and 3-acetylthio-2-ethylpropanoyl chloride for the 3-acetylthio-2-methylpropanoyl chloride in the procedure of Example 1, (±)-2,3-dehydro-1-(3-acetylthio-2-ethyl-1-oxopropyl)pipecolic acid is obtained.

EXAMPLE 23

(±)-2,3-Dehydro-1-(2-mercapto-1-oxopropyl)pipecolic acid

By substituting pipecolic acid tert-butyl ester for the L-proline tert-butyl ester in the procedure of Example 5, (±)-2,3-dehydro-1-(2-mercapto-1-oxopropyl)-pipecolic acid is obtained.

EXAMPLE 24

2,3-Dehydro-1-(3-butyrylthio-1-oxopropyl)pipecolic acid

By substituting pipecolic acid tert-butyl ester for the L-proline tert-butyl ester and 3-butyrylthiopropanoyl chloride for the 3-acetylthio-2-methylpropanoyl chloride in the procedure of Example 1, and then submitting the product to the procedure of Example 2, 2,3-dehydro-1-(3-butyrylthio-1-oxypropyl)-pipecolic acid is obtained.

EXAMPLE 25

(±)-2,3-Dehydro-1-(2-acetylthio-1-oxopropyl)-5-hydroxy-pipecolic acid

By substituting 5-tert-butoxy-L-pipecolic acid tert-butyl ester [prepared from 5-hydroxy-L-pipecolic acid by the procedure described in J. Am. Chem. Soc., 82, 3359 (1960) for L-proline] and 2-acetylthiopropanoyl chloride for the 3-acetylthio-2-methylpropanoyl chloride in the procedure of Example 1, (±)-2,3-dehydro-1-(2-acetylthio-1-oxopropyl)-5-hydroxypipecolic acid is obtained.

EXAMPLE 26

2,3-Dehydro-1-(2-mercaptoacetyl)-5-hydroxypipecolic acid

By substituting 5-tert-butoxy-L-pipecolic tert-butyl ester for the L-proline tert-butyl ester and acetylthioacetyl chloride for the 3-mercapto-2-methylpropanoyl chloride in the procedure of Example 1, and then submitting the product to the procedure of Example 2, 2,3-dehydro-1-(2-mercaptoacetyl)-5-hydroxypipecolic acid is obtained.

EXAMPLE 27

(±)-2,3-Dehydro-1-(3-mercapto-2-methyl-1-oxopropyl)-5-hydroxypipecolic acid

By substituting 5-tert-butoxy-L-pipecolic acid tert-butyl ester for the L-proline tert-butyl ester in the procedure of Example 1 and then submitting the product of the procedure of Example 2, (±)-2,3-dehydro-1-(3-mercapto-2-methyl-1-oxopropyl)-5-hydroxypipecolic acid is obtained.

EXAMPLE 28

2,3-Dehydro-5-fluoro-1-(3-mercapto-2-methyl-1-oxopropyl)pipecolic acid

By substituting 5-fluoropipecolic acid tert-butyl ester [prepared from 5-hydroxypipecolic by the procedures described in Biochemistry, 4, 2507 (1965) and in J. Am. Chem. Soc., 82, 3359 (1960) for 4-fluoro-L-proline and proline tert-butyl ester] for L-proline tert-butyl ester in the procedure of Example 1 and then submitting the product to the procedure of Example 2, 2,3-dehydro-5-fluoro-1-(3-mercapto-2-methyl-1-oxopropyl)pipecolic acid is obtained.

EXAMPLE 29

2,3-Dehydro-5-chloro-1-(2-mercaptoacetyl)pipecolic acid

By substituting 5-chloropipecolic acid tert-butyl ester [prepared from 5-hydroxypipecolic acid by the procedures described in Aust. J. Chem., 20, 1493 (1967) and in J. Am. Chem. Soc., 82, 3359 (1960) for 4-chloro-L-proline and L-proline tert-butyl ester] for L-proline tert-butyl ester and 2-acetylthioacetyl chloride for the 3-acetylthio-2-methylpropanoyl chloride in the procedure of Example 1, and then submitting the product to the procedure of Example 2, 2,3-dehydro-5-chloro-1-(2-mercaptoacetyl)pipecolic acid is obtained.

EXAMPLE 30

2,3-Dehydro-1-(3-acetylthio-1-oxopropyl)-5-methoxypipecolic acid

By substituting 5-methoxypipecolic acid methyl ester [prepared from 5-hydroxypipecolic acid by the procedure described in J. Chem. Soc. 429 (1945) for 5-methoxyproline] for the L-proline methyl ester in the procedure of Example 18, 2,3-dehydro-1-(3-acetylthio-1-oxopropyl)-5-methoxypipecolic acid is obtained.

EXAMPLE 31

2,3-Dehydro-1-(3-mercapto-1-oxopropyl)-5-methoxypipecolic acid

By substituting 5-methoxypipecolic acid tert-butyl ester for the 4-methoxy-L-proline tert-butyl ester in the procedure of Example 14, 2,3-dehydro-1-(3-mercapto-1-oxopropyl)-5-methoxypipecolic acid is obtained.

EXAMPLE 32

(±)-2,3-Dehydro-1-(3-mercapto-2-methyl-1-oxopropyl)-5-methoxypipecolic acid

By substituting 5-methoxypipecolic acid tert-butyl ester for the L-proline tert-butyl ester in the procedure of Example 1, and then submitting the product to the procedure of Example 2, (±)-2,3-dehydro-1-(3-mercapto-2-methyl-1-oxopropyl)-5-methoxypipecolic acid is obtained.

EXAMPLE 33

(±)-2,3-Dehydro-1-(3-mercapto-2-methyl-1-oxopropyl)-pipecolic acid sodium salt

By substituting (±)-2,3-dehydro-1-(3-mercapto-2-methyl-1-oxopropyl)pipecolic acid for the (±)-4,5-dihydro-1-(3-mercapto-2-methyl-1-oxopropyl)-1H-pyrrole-2-carboxylic acid in the procedure of Example 16, (±)-2,3-dehydro-1-(3-mercapto-2-methyl-1-oxopropyl)pipecolic acid sodium salt is obtained.

EXAMPLE 34

1,1'-[Dithiobis(2-methyl-1-oxopropane-3,1-diyl)]-bis-2,3-dehydropipecolic acid

By substituting (±)-2,3-dehydro-1-(3-mercapto-2-methyl-1-oxopropyl)pipecolic acid for the (±)-4,5-dihydro-1-(3-mercapto-2-methyl-1-oxopropyl)-1H-pyrrole-2-carboxylic acid in the procedure of Example 17, 1,1'-[dithiobis(2-methyl-1-oxopropane-3, 1-diyl)]bis-2,3-dehydropipecolic acid is obtained.

EXAMPLE 35

S-4,5-Dihydro-1-(3-mercapto-2-methyl-1-oxopropyl)-1H-pyrrole-2-carboxylic acid

By substituting S-3-acetylthio-2-methylpropanoyl chloride for the (±)-3-acetylthio-2-methylpropanoyl chloride in the procedure of Example 1, and then submitting the product to the procedure of Example 2, S-4,5-dihydro-1-(3-mercapto-2-methyl-1-oxopropyl)-1H-pyrrole-2-carboxylic acid is obtained.

EXAMPLE 36

1-[3-Acetylthio-1-oxopropyl]-4,5-dihydro-1H-pyrrole-2-carboxylic acid, tert-butyl ester By substituting 3-acetylthiopropanoyl chloride in the procedure of Example 1b, 1-[3-acetylthio-1-oxopropyl]-4,5-dihydro-1H-pyrrole-2-carboxylic acid, tert-butyl ester, m.p. 59°–62°, is obtained after recrystallization from hexane.

EXAMPLE 37

1-[3-Acetylthio-1-oxopropyl]-4,5-dihydro-1H-pyrrole-2-carboxylic acid

By substituting 1-[3-acetylthio-1-oxopropyl]-4,5-dihydro-1H-pyrrole-2-carboxylic acid, tert-butyl ester (Example 36) in the procedure of Example 1c, 1-[3-acetylthio-1-oxopropyl]-4,5-dihydro-1H-pyrrole-2-carboxylic acid, m.p. 89°–91° (ethyl acetate) is obtained.

EXAMPLE 38

4,5-Dihydro-1-(3-mercapto-1-oxopropyl)-1H-pyrrole-2-carboxylic acid

By substituting 1-[3-acetylthio-1-oxopropyl]-4,5-dihydro-1H-pyrrole-2-carboxylic acid (Example 37) in the procedure of Example 2, 4,5-dihydro-1-(3-mercapto-1-oxopropyl)-1H-pyrrole-2-carboxylic acid, m.p. 94°–96° (ethyl acetate) is obtained.

EXAMPLE 39

1,1'-[Dithiobis-(1-oxo-3,1-propanediyl)]bis[4,5-dihydro-1H-pyrrole-2-carboxylic acid], tert-butyl ester By substituting 3,3'-dithiodipropanoyl chloride in the procedure of Example 1b, 1,1'-[dithiobis-(1-oxo-3,1-propanediyl)]bis[4,5-dihydro-1H-pyrrole-2-carboxylic acid], tert-butyl ester is obtained as a chromatographically pure oil after chromatography on silica gel using 4:1 benzene-ethyl acetate as eluant. $R_f=0.50$ (silica gel; benzene:ethyl acetate, 1:1).

EXAMPLE 40

1,1'-[Dithiobis(1-oxo-3,1-propanediyl)]bis[4,5-dihydro-1H-pyrrole-2-carboxylic acid]

By substituting 1,1'-[dithiobis(1-oxo-3,1-propanediyl)]bis[4,5-dihydro-1H-pyrrole-2-carboxylic acid], tert-butyl ester (Example 39) in the procedure of Example 1c, 1,1'-[dithiobis(1-oxo-3,1-propanediyl)]bis[4,5-dihydro-1H-pyrrole-2-carboxylic acid, m.p. 158°–160° (ethyl acetate-methanol) is obtained.

EXAMPLE 41

1,1'-[Dithiobis(1-oxo-3,1-propanediyl)]bis[4,5-dihydro-1H-pyrrole-2-carboxylic acid], methyl ester By substituting both 1,2-dehydroproline methyl ester and 3,3'-dithiodipropanoyl chloride in the procedure of Example 1b, 1,1'-[dithiobis(1-oxo-3,1-propanediyl)]bis[4,5-dihydro-1H-pyrrole-2-carboxylic acid], methyl ester is obtained as a chromtographically pure oil after chromatography on silica gel using 4:1 benzene-ethyl acetate as eluant. $R_f=0.27$ (silica gel; benzene:ethyl acetate, 1:1).

EXAMPLE 42

(±)-1-[3-(Benzoylthio)-2-methyl-1-oxopropyl]-4,5-dihydro-1H-pyrrole-2-carboxylic acid (a)

(±)-1-[3-(Benzoylthio)-2-methyl-1-oxopropyl]-4,5-dihydro-1H-pyrrole-2-carboxylic acid, t-butyl ester Following the procedure of Example 1(b) but substituting an equivalent amount of 3-benzoylthio-2-methylpropanoyl chloride for the 3-acetylthio-2-methylpropanoyl chloride, one obtains (±)-1-[benzoylthio)-2-methyl-1-oxopropyl]-4,5-dihydro-1H-pyrrole-2-carboxylic acid, t-butyl ester.

(b)

(±)-1-[3-(Benzoylthio)-2-methyl-1-oxopropyl]-4,5-dihydro-1H-pyrrole-2-carboxylic acid The t-butyl ester product from part (a) is treated with anisole and trifluoroacetic acid according to the procedure of Example 1(c) to yield (±)-1-[3-(benzoylthio)-2-methyl-1-oxopropyl]-4,5-dihydro-1H-pyrrole-2-carboxylic acid.

EXAMPLE 43

(±)-1-[3-(Benzoylthio)-2-methyl-1-oxopropyl]-2,3-dehydro-pipecolic acid

Following the procedure of Example 1 but substituting pipecolic acid, t-butyl ester for the proline, t-butyl ester in part (a) and 3-benzoylthio-2-methylpropanol chloride for the 3-acetylthio-2-methylpropanoyl chloride in part (b), one obtains (±)-1-[3-(Benzoylthio)-2-methyl-1-oxopropyl]-2,3-dehydro-pipecolic acid.

EXAMPLE 44

(±)-4,5-Dihydro-1-[3-[(2-furanylcarbonyl)thio]-2-methyl-1-oxopropyl]-1H-pyrrole-2-carboxylic acid Following the procedure of Example 1 but substituting an equivalent amount of 3-[(2-furanylcarbonyl)thio]-2-methylpropanoyl chloride for the 3-acetylthio-2-methylpropanoyl chloride in part (b) and subjecting the product to the procedure of Example 1(c), one obtains (±)-4,5-dihydro-1-[3-[(2-furanylcarbonyl)thio]-2-methyl-1-oxopropyl]-1H-pyrrole-2-carboxylic acid.

EXAMPLE 45

(±)-4,5-Dihydro-1-[3-[(2-thienylcarbonyl)thio]-2-methyl-1-oxopropyl]-1H-pyrrole-2-carboxylic acid Following the procedure of Example 1 but substituting an equivalent amount of 3-[(2-thienylcarbonyl)-thio]-2-methylpropanoyl chloride for the 3-acetylthio-2-methylpropanoyl chloride in part (b) and subjecting the product to the procedure of Example 1 (c), one obtans (±)-4,5-dihydro-1-[3-[(2-thienylcarbonyl)thio]-2-methyl-1-oxopropyl]-1H-pyrrole-2-carboxylic acid.

EXAMPLE 46

4,5-Dihydro-1-[3-[(cyclohexylcarbonyl)thio]-1-oxopropyl]-1H-pyrrole-2-carboxylic acid Following the procedure of Example 1 but substituting an equivalent amount of 3-[(cyclohexylcarbonyl)thio]propanoyl chloride for the 3-acetylthio-2-methylpropanoyl chloride in part (b) and subjecting the product to the procedure of Example 1 (c), one obtains 4,5-dihydro-1-[3-[(cyclohexylcarbonyl)thio]-1-oxopropyl]-1H-pyrrole-2-carboxylic acid.

EXAMPLE 47

(±)-4,5-Dihydro-1-[3-[[(4-pyridino)carbonyl]thio]-2-methyl-1-oxopropyl]-1H-pyrrole-2-carboxylic acid Following the procedure of Example 1 but substituting an equivalent amount of 3-[[(4-pyridino)-carbonyl]-thio]-2-methylpropanoyl chloride for the 3-acetylthio-2-methylpropanoyl chloride in part (b) and subjecting the product to the procedure of Example 1 (c), one obtains (±)-4,5-dihydro-1-[3-[[(4-pyridino)carbonyl]-thio]-2-methyl-1-oxopropyl]-1H-pyrrole-2-carboxylic acid.

EXAMPLE 48

(±)-4,5-Dihydro-1-[3-[[(4-methylphenyl))carbonyl]thio]-2-methyl-1-oxopropyl]-1H-pyrrole-2-carboxylic acid Following the procedure of Example 1 but substituting an equivalent amount of 3-[[(4-methylphenyl)-carbonyl]thio]-2-methylpropanoyl chloride for the 3-acetylthio-2-methylpropanoyl chloride in part 1(b) and subjecting the product to the procedure of Example 1 (c), one obtains (±)-4,5-dihydro-1-[3-[[(4-methylphenyl)-carbonyl]thio]-2-methyl-1-oxopropyl]-1H-pyrrole-2-carboxylic acid.

What is claimed is:

1. A compound of the formula

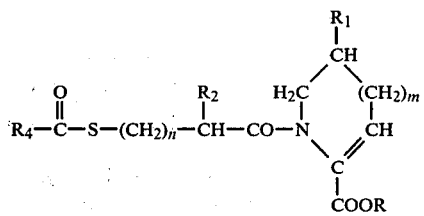

wherein

R and $R_2$ each is hydrogen or lower alkyl;
$R_1$ is hydrogen, hydroxy, halogen or lower alkoxy;
$R_4$ is lower alkyl of 1 to 6 carbons, cycloalkyl of 3 to 7 carbons,

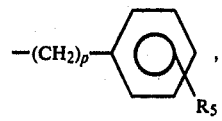

p is zero, one or two;
$R_5$ is hydrogen, lower alkyl of 1 to 4 carbons, lower alkoxy of 1 to 4 carbons, lower alkylthio of 1 to 4 carbons, or halogen;
X is O or S;
m and n each is zero or one;
and physiologically acceptable salts thereof.

2. A compound as in claim 1 wherein

is lower alkanoyl of 2 to 4 carbons or benzoyl.

3. A compound as in claim 2 wherein m is 0.

4. A compound as in claim 2 wherein m is 1.

5. A compound as in claim 3 wherein R, $R_1$ and $R_2$ each is hydrogen, and

is lower alkanoyl of 2 to 4 carbons.

6. A compound as in claim 5 wherein

is acetyl.

7. A compound as in claim 3 wherein R, $R_1$, and $R_2$ each is hydrogen,

is acetyl; and n is zero.

8. A compound as in claim 3 wherein R and $R_1$ each is hydrogen; $R_2$ is methyl;

is acetyl; and n is one.

* * * * *